US008663620B2

(12) United States Patent
Zhang et al.

(10) Patent No.: US 8,663,620 B2
(45) Date of Patent: *Mar. 4, 2014

(54) MURGANTIOL AS A STINK BUG SYNERGISTIC ATTRACTANT FOR USE OUTDOORS

(75) Inventors: Qing-He Zhang, Spokane Valley, WA (US); Rodney G. Schneidmiller, Greenacres, WA (US); Guiji Zhou, Spokane Valley, WA (US); Doreen R. Hoover, Spokane, WA (US)

(73) Assignee: Sterling International Inc., Spokane, WA (US)

( * ) Notice: Subject to any disclaimer, the term of this patent is extended or adjusted under 35 U.S.C. 154(b) by 0 days.

This patent is subject to a terminal disclaimer.

(21) Appl. No.: 13/410,124

(22) Filed: Mar. 1, 2012

(65) Prior Publication Data

US 2013/0078211 A1    Mar. 28, 2013

Related U.S. Application Data

(60) Provisional application No. 61/540,345, filed on Sep. 28, 2011.

(51) Int. Cl.
*A01N 43/04* (2006.01)
*A01P 19/00* (2006.01)
*A01M 1/02* (2006.01)

(52) U.S. Cl.
USPC .............................................. 424/84; 43/107

(58) Field of Classification Search
None
See application file for complete search history.

(56) References Cited

U.S. PATENT DOCUMENTS

| | | | |
|---|---|---|---|
| 6,387,933 B1 | 5/2002 | Nakamura | |
| 6,413,508 B1 | 7/2002 | Dickens | |
| 7,150,125 B1 | 12/2006 | Mizell, III | |
| 7,824,668 B2 | 11/2010 | McKibben | |
| 7,886,481 B2 | 2/2011 | Schneidmiller | |
| 2008/0044375 A1* | 2/2008 | McKibben | 424/84 |
| 2012/0294828 A1 | 11/2012 | Zhang | |
| 2013/0104445 A1 | 5/2013 | Schneidmiller | |

OTHER PUBLICATIONS

P. G. Tillman, J. R. Aldrich, A. Khrimian, and T. E. Cottrell. Pheromone Attraction and Cross-Attraction of Nezara, Acrosternum, and *Euschistus* spp. Stink Bugs (*Heteroptera*: Pentatomidae) in the Field. Environmental Entomology, 39(2):610-617. 2010.*
Deane K. Zahn, Jardel A. Moreira, and Jocelyn G. Millar.Identification, Synthesis, and Bioassay of a Male-Specific Aggregation Pheromone from the Harlequin Bug, *Murgantia histrionica*. J Chem Ecol (2008) 34:238-251.*
International Search Report and Written Opinion mailed Oct. 29, 2012, issued in corresponding International Application No. PCT/US2012/030393, filed Mar. 23, 2012, 7 pages.
Aldrich, J.R., et al., "Identification and Attractiveness of a Major Pheromone Component for Nearctic *Euschistus* spp. Stink Bugs (*Heteroptera*: Pentatomidae)," Environ. Entomol. 20(2):477-483, Apr. 1991.
Aldrich, J.R., et al., "Methyl 2,4,6-decatrienoates Attract Stink Bugs and Tachinid Parasitoids," J. Chem. Ecol. 33(4):801-815, Apr. 2007.
Gill, S., et al., "Brown Marmorated Stink Bug (*Halyomorpha halys*)," IPM Pest Alert, University of Maryland Extension, Oct. 2010, 4 pages.
Gill, S., et al., "The Brown Marmorated Stink Bug (*Halyomorpha halys*)," IPM Garden Center Fact Sheet, University of Maryland Extension, Mar. 2011, 4 pages.
Khrimian, A., "The Geometric Isomers of Methyl-2,4,6-decatrienoate, Including Pheromones of at Least Two Species of Stink Bugs," Tetrahedron 61(15):3651-3657, Apr. 2005.
McBrien, H.L., et al., "Sex Attractant Pheromone of the Red-Shouldered Stink Bug *Thyanta pallidovirens*: a Pheromone Blend With Multiple Redundant Components," Journal of Chemical Ecology 28(9):1797-1818, Sep. 2002.
Millar, J.G., "Methyl (2E,4Z,6Z)-Deca-2,4,6-trienoate, a Thermally Unstable, Sex-Specific Compound From the Stink Bug *Thyanta pallidovirens*," Tetrahedron Letters 38(46):7971-7972, Nov. 1997.
Millar, J.G., et al., "Pentatomid Bug Pheromones in IPM: Possible Applications and Limitations," in P. Witzgall et al. (eds.), Pheromones and Other Biological Techniques for Insect Control in Orchards and Vineyards: Proceedings of the Working Group Meeting, Samos, Greece, Sep. 25-29, 2000, IOBC WPRS Bulletin 25(9), 2002, 11 pages.
Moraes, M.C.B., et al., "Sex Attractant Pheromone From the Neotropical Red-Shouldered Stink Bug, *Thyanta perditor* (F.)," Journal of Chemical Ecology, 31(6):1415-1427, Jun. 2005.
Sugie, H., et al., "Identification of the Aggregation Pheromone of the Brown-Winged Green Bug, Plautia stali Scott (*Heteroptera*: Pentatomidae)," Appl. Entomol. Zool. 31(3):427-431, 1996.
Zahn, D.K., et al., "Identification, Synthesis, and Bioassay of a Male-Specific Aggregation Pheromone From the Harlequin Bug, *Murgantia histrionica*," J Chem Ecol 34(2):238-251, Feb. 2008.

(Continued)

*Primary Examiner* — Frederick Krass
*Assistant Examiner* — Michael P Cohen
(74) *Attorney, Agent, or Firm* — Christensen O'Connor Johnson Kindness PLLC

(57) ABSTRACT

Provided herein are uses of the Harlequin bug pheromone, murgantiol, alone or in a synergistic combination with at least one other stink bug attractant, such as methyl (2E,4E,6Z)-decatrienoate or methyl (2E,4Z)-decadienoate, or both, for attracting stink bugs such as the brown marmorated stink bug in outdoor settings. Stink bug traps comprising murgantiol, or synergistic compositions comprising murgantiol with at least one other stink bug attractant, and methods of using these compositions in traps outdoors are provided. Compositions comprising murgantiol are also described as synergistic combinations of murgantiol with at least one other stink bug attractant.

17 Claims, 3 Drawing Sheets

(56) References Cited

OTHER PUBLICATIONS

Zhang, Q-H., et al., "Murgantiol as an Indoor Stink Bug Attractant," U.S. Appl. No. 13/180,281, filed Jul. 11, 2011.

Aldrich, J.R., et al., "Semiochemically Based Monitoring of the Invasion of the Brown Marmorated Stink Bug and Unexpected Attraction of the Native Green Stink Bug (*Heteroptera*: Pentatomidae) in Maryland," Florida Entomologist 92(3):483-491, Sep. 2009.

Endo, N., et al., "Pheromonal Cross-Attraction in True Bugs (*Heteroptera*): Attraction of *Piezodorus hybneri* (Pentatomidae) to Its Pheromone Versus the Pheromone of Riptortus pedestris (Alydidae)," Environmental Entomology 39(6):1973-1979, Dec. 2010.

Gill, S., "Pest Management: The Brown Marmorated Stink Bug—Published Date Dec. 27, 2010," Growertalks, <http://www.ballpublishing.com/Growertalks/ViewArticle.aspx?articleid=18206>, Jan. 2011, vol. 74, No. 9, 3 pages.

Millar, J.G., et al., "Field Trials of Aggregation Pheromones for the Stink Bugs Chlorochroa uhleri and Chlorochroa sayi (Hemiptera: Pentatomidae)," Journal of Economic Entomology 103(5):1603-1612, Oct. 2010.

Prosecution history of U.S. Appl. No. 13/18028, filed Jul. 11, 2011.

* cited by examiner

MURGANTIOL AS A STINK BUG SYNERGISTIC ATTRACTANT FOR USE OUTDOORS

CROSS-REFERENCE TO RELATED APPLICATION

This application claims the benefit of U.S. Provisional Application No. 61/540,345, filed on Sep. 28, 2011, incorporated herein by reference in its entirety.

BACKGROUND

Pesticides, such as insecticides, are commonly used in agricultural, industrial, and residential settings to battle destructive, pestiferous, or disease-carrying insects and other animals. Pesticides have achieved significant successes in controlling pestiferous and disease-vector animals, and have increased in their lethality over the years. However, increasingly, the environmental and human health effects of pesticides, as well as their deleterious effects on beneficial insect species and other animals, have caused users to seek other means for controlling pest populations.

Pentatomoidea is a superfamily of insects that includes some of the stink bugs and shield bugs. The name "stink bug" derives from their tendency to eject an odiferous defensive substance when disturbed, typically as a form of anti-predator adaptation. The term "stink bug" is also applied to distantly related species such as *Boisea trivittata* (Say), the "boxelder bug," and insects such as beetles in the genus *Eleodes* such as the pinacate beetle (also known as the stink beetle). Many stink bugs and shield bugs are considered agricultural pest insects, although some are beneficial insects. Examples of both include the spined soldier bug, *Podisus maculiventris*; several species of *Euschistus* spp.; the red-shouldered stink bug, *Thyanta pallidovirens*; the red-banded stink bug, *Piezodorus guildinii*; the green stink bug, *Acrosternum hilare*; the kudzu bug (*Megacopta cribraria*); the conchuela stink bug, *Chlorochroa ligata*; Uhler's stink bug, *C. uhleri*; and Say's stink bug, *C. sayi*. Some insects can generate large populations that damage crop production and are resistant to many pesticides. Moreover, they are immune to genetically modified crops, such as Bt (*bacillus thuringiensis*) crops. Over the past 5-10 years, stink bugs and plant bugs have become a serious agricultural pest problem in many parts of the world, especially in the regions with large areas of Bt crops.

As an example, the brown marmorated stink bug (BMSB), *Halyomorpha halys* (Stål), native to Asia, is believed to have been accidentally introduced into the United States as early as 1996, likely as stowaways, possibly as eggs, on packing crates or the like. The BMSB has been recorded in a total of 33 states and the District of Columbia according to information provided by the U.S. Department of Agriculture and the National Agricultural Pest Information System (NAPIS) (http://pest.ceris.purdue.edu). In 2010, the BMSB emerged as a severe pest of fruit and other crops across the region. In addition, this invasive species is a serious nuisance for homeowners and businesses as it overwinters in residential houses, commercial buildings, and warehouses.

The brown marmorated stink bug can cause widespread damage to fruits, vegetables, and field crops, including peaches, apples, green beans, soybeans, corn, tomatoes, cherries, raspberries, and pears. It is a sucking insect that uses its proboscis to pierce the host plant in order to feed. This feeding may cause necrotic areas on the outer surface of fruits, leaf stippling, cat-facing on tree fruits, seed loss, and transmission of plant pathogens. Frequently, the brown marmorated stink bug survives the winter as an adult by entering structures that shield them from the elements. During the overwintering period, stink bugs are generally less active and normally aggregate in dark spaces for hibernation; however, stink bugs may awaken and move (crawl/walk/fly) around in rooms or other indoor spaces when indoor temperatures are high, especially during late winter and early spring. Such indoor activity creates various inconvenient issues (such as unpleasant smells and other annoying activities) for residents.

Aggregation pheromone compounds have been identified from many species of agriculturally important stink bugs. In 2008, Zahn et al. noted that for all phytophagous pentatomoids for which sex or aggregation pheromones have been identified, the compounds were produced by males. *J. Chem. Ecol.* 34:238 (2008). Males of *Thyanta* spp., for example, produce methyl (2E,4Z,6Z)-decatrienoate (Millar, *Tetrahedron Lett.* 38:7971 (1997); McBrien et al., *J. Chem. Ecol.* 28:1797 (2002)) with or without particular sesquiterpenes (Moraes et al., *J. Chem. Ecol.* 31:1415 (2005)) that attract a mate. J. G. Millar et al. reported findings regarding male-produced pheromone components of several agriculturally important stink bugs, including *T. pallidovirens, A. hilare, C. sayi, C. uhleri*, and *C. ligata*. *Bull. Int. Org. of Biol. Control, Pheromone Working Group* 25:1 (2002). Methyl (2E,4Z)-decadienoate (M24DD) has been identified as an aggregation pheromone compound or field attractant for seven *Euschistus* spp. (Aldrich, et al., *Environ. Entomol.* 20:477 (1991)), and has been used for stink bug monitoring programs in agricultural settings. Another methyl ester, methyl (2E,4E,6Z)-decatrienoate (M246DT), was identified as an aggregation pheromone component of the stink bug *Plautia stali* Scott (Sugie et al., *Appl. Entomol.* 31:427 (1996)), and as a field attractant for both adults (males and females) and nymphs of the BMSB, *Halyomorpha halys* (Stål) and *A. hilare* (Aldrich et al., *J. Chem. Ecol.* 33:801 (2007)); Khrimian, *Tetrahedron* 61:3651 (2005)).

Recently, a sesquiterpene epoxyalcohol, murgantiol (CAS#: 1030630-94-4), was identified by Zahn et al., *J. Chem. Ecol.* 34:238 (2008), as an aggregation pheromone component of the Harlequin bug, *Murgantia histrionica* (Hahn), and was recently found by the present inventors as an indoor attractant for BMSBs during their overwintering period indoors (U.S. patent application Ser. No. 13/180,281, filed Jul. 11, 2011). Unfortunately, it is still unknown if the Harlequin bug pheromone, murgantiol, is also attractive to Harlequin stink bugs or BMSBs or other related stink bugs outdoors during the summer mating and feeding season, or whether it is synergistically active as an attractant outdoors with known stink bug attractants, such as M246DT and M24DD for BMSB or *Euschistus* spp.

SUMMARY

In order to develop an efficient stink bug trapping system for stink bugs, especially the BMSB, the assignee of the present invention has recently invented an attractant-baited stink bug trap (U.S. patent application Ser. No. 13/331,394, filed Dec. 20, 2011; U.S. Pat. No. D645,534; and U.S. Pat. No. D645,535, each of which is incorporated herein by reference in its entirety), and a trap that features an LED light accessory (U.S. Provisional Patent Application Ser. No. 61/477,044, filed Apr. 19, 2011, incorporated herein by reference in its entirety), plus an indoor attractant for stink bugs (U.S. patent application Ser. No. 13/180,281, filed Jul. 11, 2011, incorporated herein by reference in its entirety). The present inventors have tested the Harlequin bug pheromone, murgantiol, as an attractant alone and even more importantly in synergism with known stink bug attractants, such as methyl (2E,4E,6Z)-decatrienoate (M246DT) and methyl (2E,4Z)-decadienoate (M24DD) for BMSB or *Euschistus* spp. during the summer (outdoors) mating and feeding season.

Based on the results, disclosed herein are murgantiol-containing compositions (sometimes "compositions") and methods for attracting an insect from the superfamily Pentatomoidea, such as stink bugs and shield bugs, to an outdoor predetermined location, comprising administering to the outdoor predetermined location a composition comprising one or more compounds that attract an insect from the superfamily Pentatomoidea and a synergistic amount of murgantiol, wherein the composition is active in attracting the insect to the outdoor predetermined location. In one embodiment, the insect can be an adult or nymph stink bug, such as the BMSB. Also provided is a method for attracting an insect from the superfamily Pentatomoidea, such as stink bugs, to an outdoor predetermined location, comprising administering to the outdoor predetermined location a composition comprising an effective amount of murgantiol, wherein murgantiol is active in attracting the insect to the outdoor predetermined location. In one embodiment, the insect can be an adult or nymph stink bug, such as the BMSB.

In addition, compositions that may be used in both methods are disclosed. Some compositions may include murgantiol as a synergist with other attractants, and some compositions may include murgantiol as the only attractant.

A first composition includes one or more compounds that attract an insect from the superfamily Pentatomoidea and a synergistic amount of murgantiol, wherein the murgantiol increases attraction of the insect to the composition outdoors.

The first composition may be used to attract a shield bug or stink bug.

The first composition may include one or more compounds selected from at least one of methyl (2E,4Z)-decadienoate, methyl (2E,4E,6Z)-decatrienoate, any stereoisomers thereof, or any combination thereof.

The first composition may be used to attract a brown marmorated stink bug.

The first composition may include murgantiol (CAS#: 1030630-94-4): 4-[3-(3,3-dimethyloxiran-2-yl)-1-methylpropyl]-1-methylcyclohex-2-en-1-ol, any stereoisomer thereof, or any combination of more than one stereoisomer.

The first composition may include a racemic mixture of murgantiol stereoisomers.

The first composition may include one or more 4R/S isomers of murgantiol.

The first composition may include one or more 4S/R isomers of murgantiol.

The first composition may further include an antioxidant, an oil, or any combination thereof.

A first method of attracting an insect outdoors, includes administering an effective amount of any embodiment of the first composition to an outdoor location, and attracting an insect belonging to the superfamily Pentatomoidea to the outdoor location, wherein the first composition is active in attracting the insect. In some embodiments, the insect may be a stink bug. In some embodiments, the insect may be a brown marmorated stink bug. In some embodiments, the insect may be an adult outdoors. In some embodiments, the insect may be a nymph outdoors.

A second composition may include murgantiol in an amount effective to attract an insect from the superfamily Pentatomoidea to the composition outdoors.

The second composition may be used to attract a stink bug or shield bug.

The second composition may be used to attract a brown marmorated stink bug.

The second composition may include only murgantiol as an attractant compound.

The second composition may include murgantiol: 4-[3-(3,3-dimethyloxiran-2-yl)-1-methylpropyl]-1-methylcyclohex-2-en-1-ol, any stereoisomer thereof, or any combination of more than one stereoisomer.

The second composition may include a racemic mixture of murgantiol stereoisomers.

The second composition may include one or more 4R/S isomers of murgantiol.

The second composition may include one or more 4S/R isomers of murgantiol.

The second composition may further include an antioxidant, an oil, or any combination thereof.

A second method of attracting an insect outdoors, includes administering an effective amount of any embodiment of the second composition to an outdoor location, and attracting an insect belonging to the superfamily Pentatomoidea to the outdoor location, wherein the second composition is active in attracting the insect. In some embodiments, the insect may be a stink bug. In some embodiments, the insect may be a brown marmorated stink bug. In some embodiments, the insect may be an adult outdoors. In some embodiments, the insect may be a nymph.

Capturing overwintered insects soon after they leave their overwintering indoor sites, and before their mating and oviposition period, can reduce their early season populations and minimize both damage to host plants and late season home invasions. The methods and compositions disclosed herein are effective to attract and/or trap not only these overwintered adult insects in early summer, but also their juveniles (nymphs) and new generation adults during summer and fall seasons. Such insects can include stink bugs, including the BMSB, and shield bugs.

DESCRIPTION OF THE DRAWINGS

The foregoing aspects and many of the attendant advantages of this invention will become more readily appreciated as the same become better understood by reference to the following detailed description, when taken in conjunction with the accompanying drawings, wherein.

DETAILED DESCRIPTION

Figure 1:
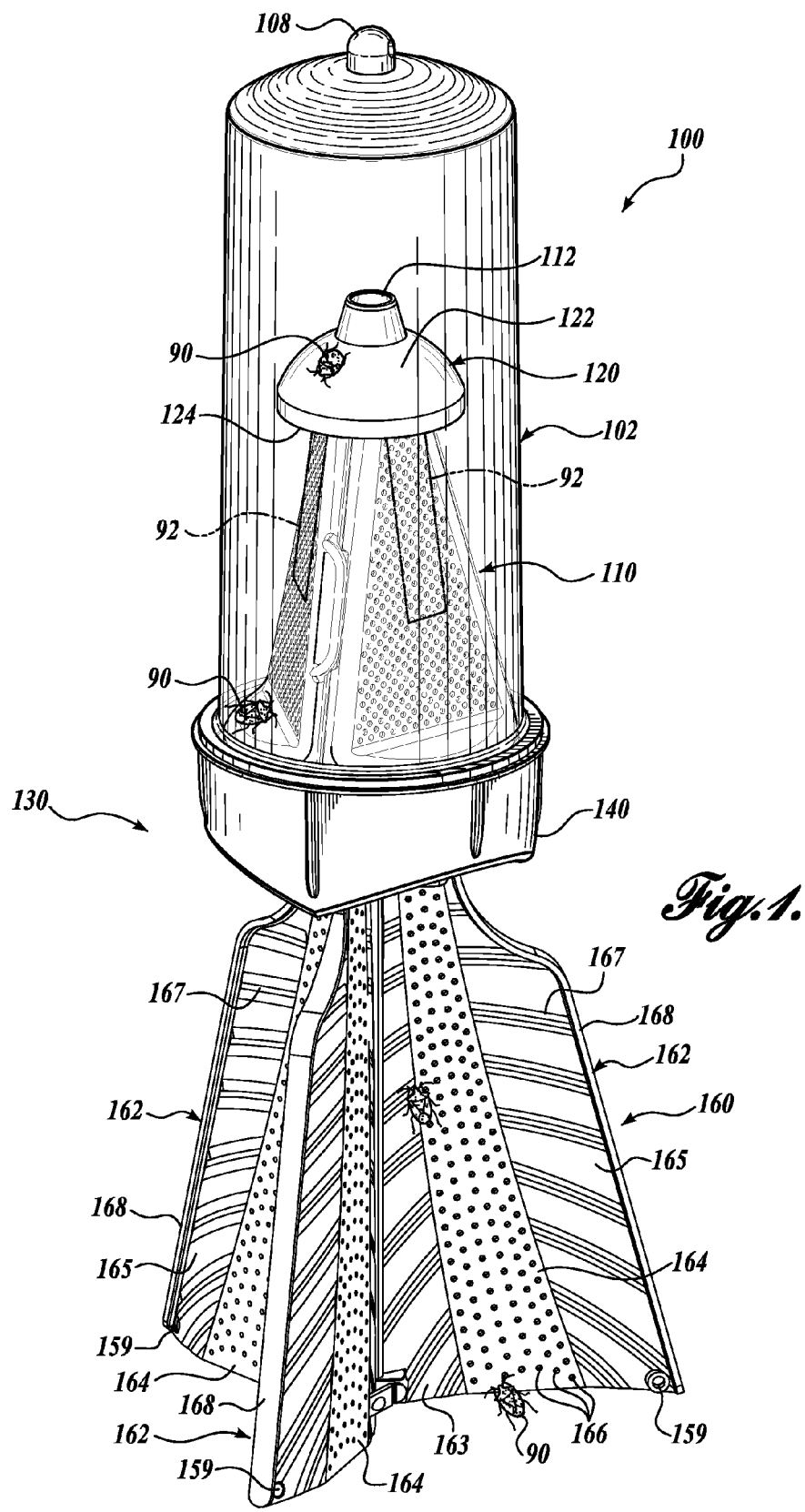
FIG. 1 is a perspective view of an insect trap that may comprise murgantiol or a synergistic composition comprising murgantiol.

Aggregation pheromone compounds have been identified from several agriculturally important stink bugs. For instance, methyl (2E,4Z)-decadienoate (M24DD) has been identified as an aggregation pheromone compound or field attractant for seven *Euschistus* spp. (Aldrich, et al., *Environ. Entomol.* 20:477 (1991)), and has been used for stink bug monitoring programs in agricultural settings. Another methyl ester, methyl (2E,4E,6Z)-decatrienoate (M246DT), was identified as an aggregation pheromone compound of the stink bug *Plautia stali* Scott (Sugie et al., *Appl. Entomol.* 31:427 (1996)) in Japan and, recently as a field attractant for both adults (males and females) and nymphs of the BMSB, *Halyomorpha halys* (Stål) and *A. hilare* (Aldrich et al., *J. Chem. Ecol.* 33:801 (2007)); Khrimian, *Tetrahedron* 61:3651 (2005)). Recently, both pheromone attractants have been used together or alone in commercial stink bug traps for monitoring or mass-trapping some stink bug species: *Euschistus* spp., BMSBs and *A. hilare* in the United States. In case of the BMSB, M246DT is strongly attractive to both nymphs and adults during the mid-summer and early fall, but is only weakly active in the late spring and early summer when the dispersal (overwintered) adults are looking for mates and oviposition sites. Thus, more powerful attractant compositions are needed to efficiently capture overwintered BMSB adults before their mating and oviposition in order to reduce their early season populations and minimize both damage to host plants and late season home invasions. The methods and compositions disclosed herein are effective to attract and/or trap not only these overwintered adult insects in early summer, but also their juveniles (nymphs) and new generation adults during summer and fall seasons. Such insects include stink bugs, including the BMSB, and shield bugs.

Recently, a sesquiterpene epoxyalcohol, murgantiol, was identified as an aggregation pheromone compound of the Harlequin bug, *Murgantia histrionica* (Hahn) (Zahn et al., *J. Chem. Ecol.* 34:238 (2008)). As reported by Zahn et al., sexually mature male Harlequin bugs produce a sex-specific compound, identified as one of the stereoisomers of the sesquiterpene epoxyalcohol: 4-[3-(3,3-dimethyloxiran-2-yl)-1-methylpropyl]-1-methylcyclohex-2-en-1-ol (murgantiol). In laboratory bioassays by Zahn et al., insect-produced and synthetic murgantiol attracted sexually mature Harlequin bugs of both sexes, suggesting that murgantiol is a male-produced aggregation pheromone analogous to those found in a number of other phytophagous bug species. No data have yet been reported on potential behavioral activity (attraction) of this compound on Harlequin bugs or other stink bugs in the field. However, murgantiol, the reported pheromone for the Harlequin bug, was recently found to be an indoor attractant for stink bugs, such as both sexes of BMSB adults during the overwintering and transition periods (U.S. patent application Ser. No. 13/180,281, filed Jul. 11, 2011).

Using recently developed Rescue!® Stink Bug Traps (U.S. Pat. No. D645,534; U.S. Pat. No. D645,535; U.S. patent application Ser. No. 13/331,394, filed Dec. 20, 2011; and U.S. Provisional Patent Application Ser. No. 61/477,044, filed Apr. 19, 2011), the present inventors discovered that the Harlequin bug pheromone, murgantiol, is also active as an outdoor attractant for the BMSBs during the summer mating/oviposition and feeding season. Further, murgantiol, together with known stink bug attractants such as M246DT and M24DD, was found to synergistically attract BMSB and *Euschistus* spp. Addition of murgantiol to known stink bug attractant systems, such as attractant-baited stink bug traps, would strengthen the efficacy of these systems for combating stink bug problems, especially ones caused by the BMSB. It is not known if the murgantiol is produced by the BMSB males as part of its aggregation pheromone system or not.

Figure 3:
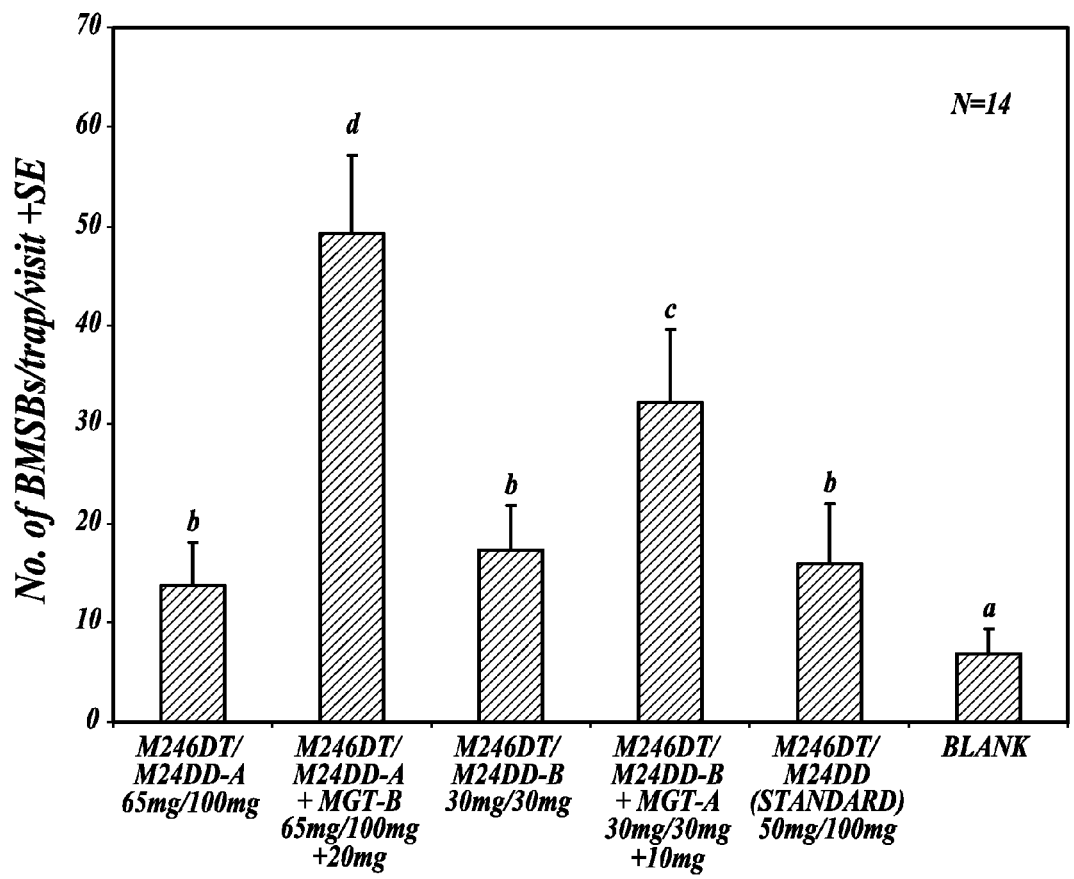
FIG. 3 is a bar graph illustrating mean numbers of BMSB adults captured in stink bug traps baited with known standard stink bug attractants (M246DT/M24DD) and two new types of stink bug attractant formulations, M246DT/24DD-A and M246DT/24DD-B, with or without different doses of racemic MGT in comparison with a blank control, in Pittsburgh, Pa., 14 days in early September [bars with the same letter were not significantly different (P>0.05) by Duncan's multiple-range test after ANOVA on arcsin(p)$^{1/2}$ transformed data; p is the proportion of total captured BMSBs within each replicate].

Provided herein are methods for attracting an insect belonging to the superfamily Pentatomoidea, and especially stink bugs such as the BMSB, to an outdoor predetermined location, comprising administering to the outdoor predetermined location a composition comprising one or more compounds that attract an insect from the superfamily Pentatomoidea and a synergistic amount of murgantiol, wherein the composition is active in attracting the insect to the outdoor predetermined location. In another embodiment, the composition comprises murgantiol as the only attractant employed. In some embodiments, the insect is a stink bug or shield bug. In some embodiments, the insect is an overwintered adult stink bug, a juvenile (nymph), or a new generation adult stink bug, including the BMSB. In some embodiments, the insect is from the genus *Euschistus*. In some embodiments, the insect is the BMSB. In some embodiments, an attractant composition may comprise M246DT or M24DD, their related stereoisomers, or any combination thereof, and murgantiol in a synergistic amount that significantly increases the attraction of the insect to the composition. FIG. 3 illustrates embodiments showing a significant increase in attraction as measured by trap catches. For example, a comparison between the first sample with the second and the third sample with the fourth shows that murgantiol produces significant increases in attraction. In some embodiments, the attractant composition may include only murgantiol in an amount that attracts the insect to the composition. The predetermined location may be a stink bug trap (e.g., an outdoor stink bug trap). Stink bug traps are further described herein. The composition may be comprised in a type of device(s) or dispenser(s) that controllably releases the composition. An attractant composition may further comprise an antioxidant or an oil, or a combination thereof, as described herein.

Murgantiol may be obtained synthetically as described by Zahn et al., *J. Chem. Ecol.* 34:238 (2008). Murgantiol is a compound with four chiral centers and 16 possible stereoisomers. The relative and absolute configurations of the insect-produced compound were not identified by Zahn et al. and are presently unknown, but the structure was reported as follows, with carbon numbering shown:

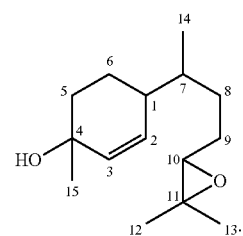

As used herein, "murgantiol" refers to any compound or mixture of compounds (isomers) that exhibit the murgantiol skeleton structure noted above. Thus, murgantiol may refer to a single isomer, a mixture of all 16 isomers (racemic murgantiol), or a mixture of any number of these isomers (e.g., a mixture of 2, 3, 4, 5, 6, 7, 8, 9, 10, 11, 12, 13, 14, or 15 isomers, or a mixture of at most or at least 2, 3, 4, 5, 6, 7, 8, 9, 10, 11, 12, 13, 14, or 15 isomers). Murgantiol may comprise a racemic mixture of stereoisomers. Murgantiol may, for example, entail one or more of the more polar isomers, such as the 4R/S-isomers (4R/S-1S-7S-10S-isomer, 4R/S-1R-7S-10S-isomer, 4R/S-1R-7R-10S-isomer, 4R/S-1R-7R-10R-isomer, 4R/S-1S-7R-10R-isomer, 4R/S-1S-7R-10S-isomer, 4R/S-1S-7S-10R-isomer, and the 4R/S-1R-7S-10R-isomer). Murgantiol may, for example, entail one or more of the less polar isomers, such as the 4S/R-isomers (4S/R-1S-7S-10S-isomer, 4S/R-1R-7S-10S-isomer, 4S/R-1R-7R-10S-isomer, 4S/R-1R-7R-10R-isomer, 4S/R-1S-7R-10R-isomer, 4S/R-1S-7R-10S-isomer, 4S/R-1S-7S-10R-isomer, and the 4S/R-1R-7S-10R-isomer). Murgantiol may entail four isomers, such as the 4R/S-7R/S-isomers (4R/S-7R/S-1R-10R-isomer, 4R/S-7R/S-1R-10S-isomer, 4R/S-7R/S-1S-10S-isomer, and the 4R/S-7R/S-1S-10R-isomer); the 4R/S-7S/R-isomers (4R/S-7S/R-1R-10R-isomer, 4R/S-7S/R-1R-10S-isomer, 4R/S-7S/R-1S-10S-isomer, and the 4R/S-7S/R-1S-10R-isomer); the 4S/R-7R/S-isomers (4S/R-7R/S-1R-10R-isomer, 4S/R-7R/S-1R-10S-isomer, 4S/R-7R/S-1S-10S-isomer, and the 4S/R-7R/S-1S-10R-isomer); and the 4S/R-7S/R-isomers (4S/R-7S/R-1R-10R-isomer, 4S/R-7S/R-1R-10S-isomer, 4S/R-7S/R-1S-10S-isomer, and the 4S/R-7S/R-1S-10R-isomer). In some embodiments, murgantiol is further defined as a mixture of diastereomers of 4-[(1S)-3-(3,3-dimethyloxiran-2-yl)-1-methylpropyl]-1-methylcyclohex-2-en-1-ol [(S)-murgantiol; CAS#: 1030630-97-7]. In some embodiments, murgantiol is further defined as a mixture of diastereomers of 4-[(1R)-3-(3,3-dimethyloxiran-2-yl)-1-methylpropyl]-1-methylcyclohex-2-en-1-ol [(R)-murgantiol].

In some embodiments, a composition comprises an isolated mixture defined as a more polar mixture of murgantiol stereoisomers obtained and separated from a racemic mixture, such as a more polar mixture of murgantiol stereoisomers (4R/S-isomers). In some embodiments, a composition comprises an isolated mixture defined as a less polar mixture of murgantiol stereoisomers obtained and separated from a racemic mixture, such as a less polar mixture of murgantiol stereoisomers (4S/R-isomers). The "more polar mixture" and the "less polar mixture" can be obtained and separated from a racemic mixture of murgantiol by flash chromatography on silica gel, eluting with 10% ethyl acetate in hexane, with the first fraction being the less polar murgantiol mixture and the later eluting fraction being the more polar murgantiol mixture. Each fraction includes 8 isomers that are inseparable by the flash chromatography. As noted herein, a composition may comprise either the 8 less polar isomers or the 8 more polar isomers. In some embodiments, a composition comprises a racemic mixture of murgantiol stereoisomers (all 16 stereoisomers).

As used herein, an "effective amount" of murgantiol is an amount effective to achieve a desired result, such as to attract an insect to an outdoor predetermined location, such as a trap that is outdoors. The effective amount of murgantiol, when used alone or as a synergistic combination with other attractant compositions, may be determined experimentally. For example, both an effective amount, and a synergistic amount of murgantiol can be at least or at most 0.01, 0.1, 10, 20, 30, 40, 50 60, 70, 80, 90, 100, 200, 300, 400, or 500 mg of murgantiol, and any range derivable therein. While representative amounts have been provided to illustrate exemplary embodiments, it is believed that any amount of murgantiol will be effective to attract insects, and to increase the attraction of other known attractants. Murgantiol may be used in a composition as the only attractant compound or in a composition further comprising one or more different attractants, semiochemicals, oils, antioxidants, or other additives, or any combination thereof.

As used herein, a "synergistic amount" of murgantiol refers to an amount that significantly increases the attraction effects of other attractant compounds.

A first composition includes one or more compounds that attract an insect from the superfamily Pentatomoidea, and a synergistic amount of murgantiol, wherein the murgantiol significantly increases attraction of the insect to the composition outdoors. FIG. 3 illustrates embodiments showing a significant increase in attraction as measured by trap catches. For example, a comparison between the first sample with the second and the third sample with the fourth shows that murgantiol produces significant increases in attraction. The first composition may be used to attract an insect from one species of shield bug or stink bug. The first composition may include murgantiol in any amount. The first composition may include one or more compounds selected from at least one of methyl (2E,4Z)-decadienoate, methyl (2E,4E,6Z)-decatrienoate, any stereoisomers thereof, or any combination thereof. The first composition may be used to attract a brown marmorated stink bug. The first composition may include murgantiol: 4-[3-(3,3-dimethyloxiran-2-yl)-1-methylpropyl]-1-methylcyclohex-2-en-1-ol, any stereoisomer thereof, or any combination of more than one stereoisomer. The first composition may include a racemic mixture of murgantiol stereoisomers. The first composition may include one or more 4R/S isomers of murgantiol. The first composition may include one or more 4S/R isomers of murgantiol. The first composition may further include an antioxidant, an oil, or any combination thereof.

A first method of attracting an insect outdoors, includes administering an effective amount of any embodiment of the first composition to an outdoor location, and attracting an insect belonging to the superfamily Pentatomoidea to the outdoor location, wherein the first composition is active in attracting the insect. In some embodiments, the insect may be a stink bug. In some embodiments, the insect may be a brown marmorated stink bug. In some embodiments, the insect may be an overwintered adult during spring or early summer outdoors. In some embodiments, the insect may be a juvenile (nymph) or new generation adult stink bug during summer and fall seasons outdoors.

Figure 2:
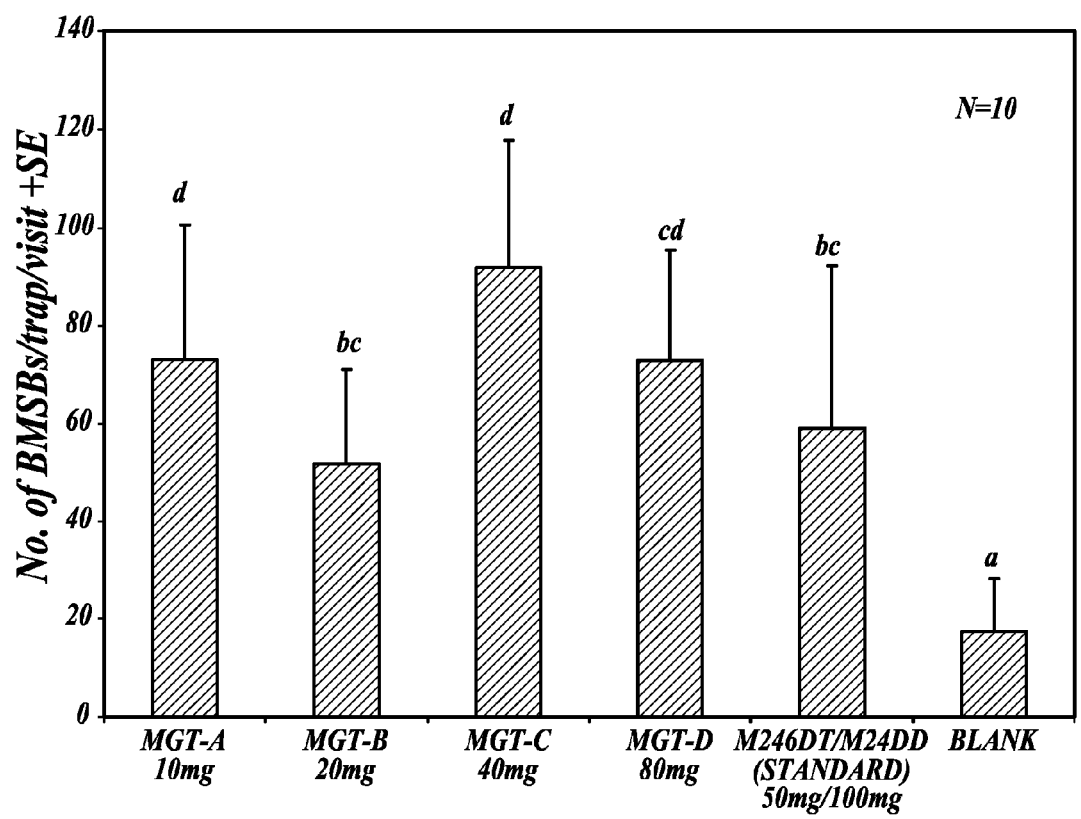
FIG. 2 is a bar graph illustrating mean numbers of BMSB adults captured in stink bug traps baited with different doses of racemic murgantiol (MGT) in comparison with the known standard stink bug attractants (M246DT/M24DD) and a blank control, in Pittsburgh, Pa., 14 days in early September [bars with the same letter were not significantly different (P>0.05) by Duncan's multiple-range test after ANOVA on arcsin $(p)^{1/2}$ transformed data; p is the proportion of total captured BMSBs within each replicate]

A second composition may include murgantiol in an amount effective to attract an insect from the superfamily Pentatomoidea to the composition outdoors. FIG. 2 illustrates embodiments showing the effectiveness in attraction as measured by trap catches. The first through fourth samples used varying amounts of murgantiol. FIG. 2 shows that murgantiol is comparable, if not more effective in attracting insects when compared to the standard M246DT/M24DD. The second composition may be used to attract a stink bug or shield bug. The second composition may be used to attract a brown marmorated stink bug. The second composition can include murgantiol in any amount. The second composition may include only murgantiol as an attractant compound. The second composition may include murgantiol: 4-[3-(3,3-dimethyloxiran-2-yl)-1-methylpropyl]-1-methylcyclohex-2-en-1-ol, any stereoisomer thereof, or any combination of more than one stereoisomer. The second composition may include a racemic mixture of murgantiol stereoisomers. The second composition may include one or more 4R/S isomers of murgantiol. The second composition may include one or more 4S/R isomers of murgantiol. The second composition may further include an antioxidant, an oil, or any combination thereof.

A second method of attracting an insect outdoors includes administering an effective amount of any embodiment of the second composition to an outdoor location and attracting an insect belonging to the superfamily Pentatomoidea to the outdoor location, wherein the second composition is active in attracting the insect. In some embodiments, the insect may be a stink bug. In some embodiments, the insect may be a brown marmorated stink bug. In some embodiments, the insect may be an overwintered adult during spring or early summer outdoors. In some embodiments, the insect may be a juvenile (nymph) or new generation adult stink bug during summer and fall seasons outdoors.

The compositions may "consist essentially" of a synergistic amount of murgantiol and one or more different attractants, or murgantiol as the only attractant. Such compositions include the specified compounds and those compounds that do not materially affect the basic and novel characteristics of the composition. For example, antioxidants, oils, and impurities may be comprised in such compositions.

The compositions may "consist" of a synergistic amount of murgantiol and one or more different attractants, or murgantiol as the only attractant. Such compositions include only the specified compounds, and exclude all other compounds.

Various additives may be combined with the compositions, including, but not limited to, antioxidants and oils. Suitable antioxidants for use with any of the murgantiol-containing compositions include, but are not limited to, tocopherols, α-tocopherol, ascorbic acid, as well as synthetic antioxidants such as propyl gallate, tertiary butylhydroquinone, butylated hydroxytoluene (BHT), and butylated hydroxyanisole (BHA). BHT or BHA, among other similar antioxidant compounds, are soluble in most of the compositions and can react efficiently with oxygen in the dispensing systems, and therefore offer a way to avoid oxidation, breakdown, and polymerization of the compositions. One class of antioxidants are lipophilic (fat-soluble) organic compounds that are primarily used as antioxidant food additives.

Suitable antioxidants also include polar antioxidants, such as phenolic alcohols, flavonoids, catechins, anthocyanins, and their glycosides. The polar phenolics are advantageous for stabilization of polar compounds.

While representative oxidants have been listed for purposes of illustrating embodiments of the invention, it is to be appreciated that other antioxidants not specifically listed above may also be used.

Suitable oils to use with murgantiol-containing compositions include, but are not limited to, oils derived from plants such as vegetable oils and nut oils. These are widely available and cost effective. Suitable oils include, but are not limited to, canola oil, cottonseed oil, palm oil, safflower oil, soybean oil, corn oil, olive oil, peanut oil, sunflower oil, sesame oil, nut oils, and coconut oils, among many others. Nut oils include, but are not limited to, almond oil, cashew oil, hazelnut oil, macadamia oil, mongongo nut oil, pecan oil, pine nut oil, pistachio oil, sacha inchi oil, and walnut oil, plus many others. Melon and gourd seed oils are very common and inexpensive. The oils listed above include saturated, monounsaturated, and polyunsaturated fatty acids that are soluble in many compositions, especially the less polar or non-polar ones.

While representative oils have been listed for purposes of illustrating embodiments of the invention, it is to be appreciated that other oils not specifically listed above may also be used.

The oils and antioxidants can be combined with murgantiol and other attractants for stabilizing murgantiol and the attractants against oxidation or for controlling the release rate from a dispenser.

Insects in the Pentatomoidea superfamily include stink bugs and shield bugs. Stink bugs are in the Pentatomidae family. Any one or more of insects from the superfamily Pentatomoidea might be attracted to the disclosed compositions. Particularly, any one or more stink bugs disclosed herein may be attracted to a murgantiol-containing composition. A variety of stink bugs are known in the art. Non-limiting examples of stink bugs include the green stink bug (*Acrosternum hilare* (Say)); several species of *Euschistus* spp. such as the brown stink bug (*Euschistus servus* (Say)), *E. tristigmus, E. conspersus, E. variolarius, E. politus,* or *E. heros*; the southern green stink bug (*Nezara viridula* (L.)); the eastern green stink bug (*Nezara antennata*); the spined soldier bug (*Podisus maculiventris*); the brown marmorated stink bug (*Halyomorpha halys*); the red-shouldered stink bug (*Thyanta pallidovirens*); the globular stink bug (*Megacopta punctatissimum*); the white-spotted stink bug (*Eysarcoris ventralis*); the fruit-piercing stink bug (*Glaucias subpunctatus*); the red-banded stink bug, *Piezodorus guildinii*; the red-striped stink bug (*Graphosoma rubrolineatum*); the East Asian stink bug (*Halyomorpha mista*); the rice stink bug (*Lagynotomus elongates, Oebalus pugnax*); the two-spotted stink bug (*Perillus bioculatus*); the conchuela stink bug (*Chlorochroa ligata*); Uhler's stink bug (*Chlorochroa uhlerii*); Say's stink bug (*Chlorochroa sayi*); the brown-winged green stink bug (*Plautia stali* (Scott)); the boxelder bug (*Boisea trivittata* (Say)); *Banasa dimidiata* (Say); *B. calva* (Say); *B. euchlora* Stål; the kudzu bug (*Megacopta cribraria*); and the Harlequin bug (*Murgantia histrionica*).

Compositions comprising a synergistic amount of murgantiol with other attractants and compositions that include murgantiol as the only attractant may be used to attract nymphs and both sexes of adult stink bugs. In some embodiments, the stink bug is the brown marmorated stink bug (BMSB).

Populations of BMSBs can cause widespread damage to fruits, vegetables, and field crops including peaches, apples, green beans, soybeans, corn, tomatoes, cherries, raspberries, and pears. The BMSB is a sucking insect that uses its proboscis to pierce the host plant in order to feed. This feeding may cause necrotic areas on the outer surface of fruits, leaf stippling, cat-facing on tree fruits, seed loss, and transmission of plant pathogens. Frequently, BMSBs survive the winter indoors as adults by entering structures that shield them from the elements. Initially, they may go inside a structure, such as a house, to hibernate, but then become more animated due to the warmth of the structure. Adults typically begin overwintering at the end of September or early October and become a nuisance as large numbers congregate and invade buildings in search of overwintering sites. The indoor period is followed by an outdoor period. It is during the outdoor period that stink bugs, such as the BMSB, will feed and/or look for water/food and oviposition sites. It is during the outdoor period that the disclosed compositions are effective in controlling the insects by attracting the insects to the compositions, and particularly when the compositions are used in combination with traps.

The murgantiol-containing compositions may be disposed in any trap suitable for stink bug trapping outdoors when the stink bugs are experiencing their outdoor period. "Outdoors" includes any location where stink bugs in their "outdoor" period may be found, such as, but not limited to, fences, decks, vegetable gardens, fruit trees, ornamental trees, orchards, nurseries, agricultural crop fields, gardens, etc.

In some embodiments, an outdoor stink bug trap includes one or more dispensers for holding and releasing compositions comprising murgantiol with one or more different stink bug attractants, such as M246DT and/or M24DD, or murgantiol alone. Non-limiting examples of stink bug traps are described in U.S. Pat. No. D645,534; U.S. Pat. No. D645,535; U.S. patent application Ser. No. 13/331,394, filed Dec. 20, 2011; U.S. Provisional Patent Application No. 61/477,044, filed Apr. 19, 2011, and U.S. Pat. No. 7,150,125, as well as Florida traps (see, e.g., Mizell and Tedders, *Proc. Southeast Pecan Growers Assoc.* 90:52 (1990)), wherein each reference is incorporated by reference in its entirety.

A non-limiting example of a stink bug trap is shown in FIG. 1. FIG. 1 is a perspective view of an insect trap 100 particularly suited for capturing insects, such as stink bugs 90, for example, brown marmorated stink bugs.

The trap 100 comprises an upper entrapment chamber 102, which in this embodiment is a generally cylindrical member that is open at a bottom end and closed at a top end. However, it will be readily apparent that the entrapment chamber may be alternatively shaped. The top end may optionally include a nib 108 to facilitate securing the trap 100 at a desired outdoor location. The entrapment chamber 102 may be formed from a transparent or translucent material to permit light to enter the entrapment chamber. It is also contemplated that the color of the entrapment chamber 102 will preferably be selected to attract the target species of insect. For example, it is known that the BMSB may be particularly attracted to green or blue, or other dark colors, and this information may be exploited when constructing traps.

An inner cone 110 is disposed in the entrapment chamber 102. The cone 110 tapers from a large opening at the bottom end disposed near the entrapment chamber bottom end to a small opening at the top end disposed inside the entrapment chamber 102. A collar 120 is attached over a top end of the cone 110. The collar 120 in this embodiment includes a hemispherical upper portion 122 with a top edge that engages the cone 110 at a solid surface thereon and a lower edge 124 that extends away from the cone 110. Preferably, the surface of the hemispherical upper portion 122 is provided with a slippery or non-stick surface to facilitate the target insects 90 falling to the bottom of the entrapment chamber 102 and to prevent insects 90 from crawling back out of the trap 100. For example, the upper portion 122 may include a layer of polytetrafluoroethylene powder (e.g., with a particle size of 0.1 to 3.0 microns) such as that marketed under the trade names Teflon® or Fluon®.

A lower base portion 130 of the trap 100 includes an annular lid 140 that is releasably attached to the entrapment chamber 102 and a vane assembly 160 assembled from a plurality of panels or vanes 162 (three shown) that extend downwardly from the annular lid 140. The annular lid 140 allows the insects 90 to enter the bottom end of the cone 110.

As illustrated in phantom in FIG. 1, one or more packets 92 containing the attractant compositions are enclosed within the entrapment chamber 102, on the exterior of the cone 110, the purpose of which is to entice the insects 90 to crawl up through the interior of the cone 110 and exit the open top end of the cone 110. The attractant compositions disposed in the trap are typically packaged, formulated, or otherwise adapted to release gradually over time. Thus, in an exemplary embodiment, the compositions are containerized in a polymer package, although other controlled release dispensers or devices may alternatively be used.

The compositions may be murgantiol alone or a murgantiol-containing synergistic composition, as described herein. More generally, the compositions may, for example, be disposed within the entrapment chamber 102, such as in a controlled release dispenser or device, between the cone 110 and the wall of the cylinder.

The trap 100 includes vanes 162 that are designed with particular features to take advantage of the stink bug's 90 behavioral tendencies. Stink bugs 90, for example, tend to alight on a surface such as the ground and to climb. For example, they may approach and even strike a vane 162 causing them to land at the base of the vane 162. The vanes 162 are designed to encourage the insect 90 to climb the vane 162 and to enter the entrapment chamber 102.

The vane assembly 160 may include three vanes 162, each curved in horizontal cross section to provide a more natural and organic shape that will be more inviting to the insect 90. For example, the vanes 162 may each be curved about a vertical axis. The vanes 162 may include a center portion 164 that is substantially planar, an inner portion 163 extending radially inward from the center portion 164, and an outer portion 165 extending radially outward from the center portion 163, wherein the inner and outer portions 163, 165 are curved in horizontal cross section.

The vanes 162 are further provided with surface features that encourage and facilitate climbing. For example, the center portions 164 are provided with a plurality of apertures that extend along the length of the vane 162 from top to bottom. The apertures facilitate climbing by providing a perch for the insects 90 and also permit air and light to penetrate, again providing a more organic-mimicking environment to encourage continued climbing. The inner portion 163 and outer portion 165 of each vane 162 further include a plurality of surface ridges 167 that extend generally radially from the center portion 164 to the inner and outer edges of the vane 162. The ridges 167 generally mimic a leaf vein structure and further facilitate climbing the vane 162 and gently encourage the insects 90 toward the center portion 164. The outer edge of each vane 162 is further provided with a flange 168 perpendicular to the vane 162, such that climbing insects 90 are directed upwardly. When an insect 90 reaches the top of the vane assembly, the insect 90 may pass through the annular lid 140 and into the bottom interior of the cone 110.

Optionally, the vanes 162 may further comprise means for fixing the trap 100 at a particular location. For example, apertures 159 in the lower outside corners of each vane 162 may be provided with a string, cable, tie wrap, or the like (not shown) that can be secured to a fixed object, such as a portion of a tree, a pipe, etc.

It is to be understood that the trap 100 of FIG. 1 is only exemplary and not limiting.

It is contemplated that any embodiment discussed in this specification can be implemented with respect to any method(s) and composition(s) described, and vice versa. Furthermore, compounds and compositions of the invention can be used to achieve methods. Moreover, in any embodiment herein, one or more elements or compounds may be omitted, substituted for another element or compound, or combined with additional elements or compounds. For example, any murgantiol-containing composition, including synergistic compositions, may be employed with any method or trap disclosed herein.

The use of the term "or" in the claims is used to mean "and/or" unless explicitly indicated to refer to alternatives only or the alternatives are mutually exclusive, although the disclosure supports a definition that refers to only alternatives and "and/or."

The use of the word "a" or "an" when used in conjunction with the term "comprising" in the claims and/or the specification may mean "one," but it is also consistent with the meaning of "one or more," "at least one," and "one or more than one."

EXAMPLES

Outdoor Behavioral Response of the Brown Marmorated Stink Bugs to the Harlequin Bug Pheromone, Murgantiol, Alone and With Other Stink Bug Pheromone Attractants Two field trapping experiments were carried out from early to late September in home gardens/yards in Pittsburgh, Pa. In order to test the potential activity of the Harlequin bug pheromone, murgantiol, as a BMSB outdoor attractant or outdoor synergistic attractant to other known stink bug attractants, commercially available Rescue!® Stink Bug Traps (described in U.S. Pat. No. D645,534; U.S. Pat. No. D645,535; and U.S. patent application Ser. No. 13/331,394, filed Dec. 20, 2011) were used. Traps baited with different tested compounds or combinations were set up in lines, 1-1.5 m above the ground on either tree branches or fences ca. 3-5 m apart between each trap within a set, and at least 50 m between sets. For each trapping experiment, five sets of traps (i.e., five physical replicates of each treatment) were deployed with their initial trap positions within each set being randomized. To minimize positional effects and obtain more replications, stink bug collections and trap re-randomizations were carried out when ≥20 stink bugs were caught in the best traps. Each replicate lasted one to several days depending on stink bug activity. Captured stink bugs were removed from the traps and kept in plastic (polyethylene) zip-bags before returning to the laboratory for recording of the species, gender, and development status (nymphs, adult males/females), and catch. Murgantiol and the known stink bug attractants were released from dispensers [for example, 4 mil polyethylene bags (2.3× 5.5 cm) or dispensers described in U.S. patent application Ser. No. 13/206,244, filed Aug. 9, 2011, incorporated herein by reference in its entirety].

Experiment 1 (Example 1) tested different doses of racemic murgantiol (MGT) in comparison with the known standard stink bug attractants [M246DT/M24DD], and the blank control.

Experiment 2 (Example 2) tested two new types of stink bug attractant formulations [M246DT/M24DD-A and M246DT/M24DD-B], with and without the racemic murgantiol (MGT-A, and MGT-B) as a potential synergist, in comparison with the known standard stink bug attractants [M246DT/M24DD], and the blank control.

Racemic murgantiol was synthesized based on the methods described by Zahn et al., *J. Chem. Ecol.* 34:238 (2008). The following scheme outlines the method starting from citronellal to prepare a racemic mixture of stereoisomers:

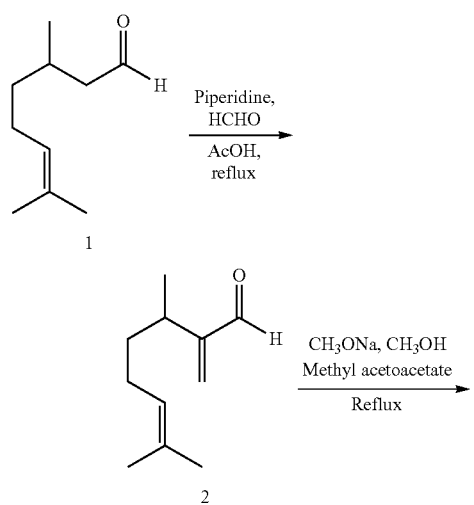

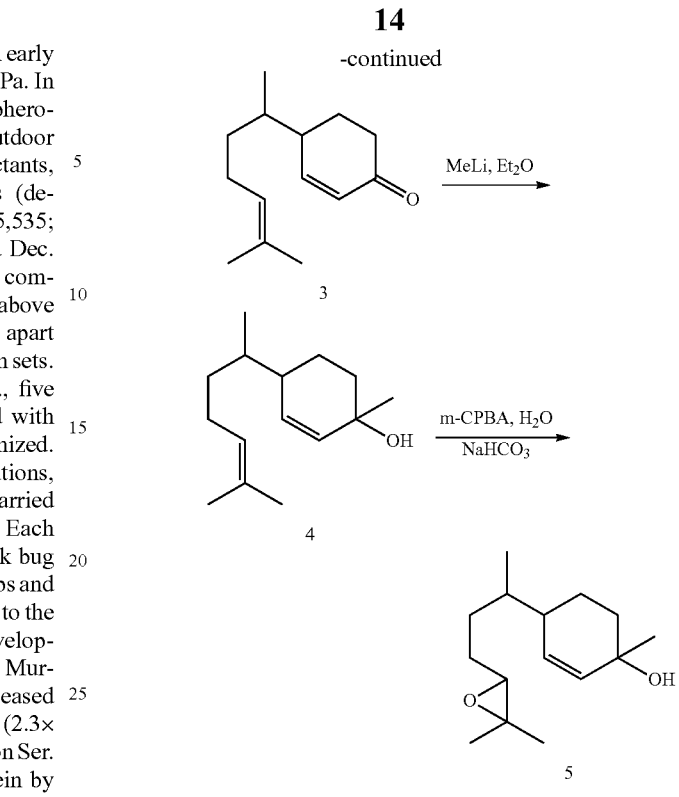

Trap catch data were converted to proportion (P) of total captured bugs within each replicate. The data were then transformed by arcsin $(P)^{1/2}$ to meet the assumptions of normality and homogeneity of variances for ANOVA (analysis of variance). Means were compared by ANOVA followed by the Duncan's multiple range test at α=0.05.

As shown in FIG. 2 (Example 1), the known standard stink bug attractants (M246DT/M24DD: 50 mg/100 mg) showed significant attraction to the BMSB adults. Progressively higher doses of racemic murgantiol (MGT), designated as MGT-A, (10 mg), MGT-B (20 mg), MGT-C (40 mg), and MGT-D (80 mg), also showed strong attraction to BMSBs at levels similar or even higher than the known standard stink bug attractants (M246DT/M24DD: 50 mg/100 mg). There were no significant dose-response effects of racemic murgantiol; and the minimum dose (MGT-A: 10 mg) was as effective as the highest dose (MGT-D: 80 mg) in trap catches. Thus, murgantiol alone is an outdoor attractant for BMSBs in any dose amount. Both sexes of adults (ca. 1:1) and nymphs were attracted and captured in traps baited with either murgantiol (MGT) or M246DT/M24DD. During this time, the number of nymphs captured was only 5% of total catches.

As shown in FIG. 3 (Example 2), the two new types of stink bug attractant formulations (M246DT/M24DD-A: 65 mg/100 mg) and M246DT/M24DD-B 30 mg/30 mg) showed significant attractions to BMSBs at the same level as the known standard stink bug attractant formulation (M246DT/M24DD: 50 mg/100 mg). However, the addition of murgantiol-B (MGT-B: 20 mg) to M246DT/M24DD-A (65 mg/100 mg) and murgantiol-A (MGT-A: 10 mg) to M246DT/M24DD-B (30 mg/30 mg) increased trap catches of BMSBs in a synergistic fashion. This result indicated that murgantiol can significantly increase the effectiveness of the known stink bug attractants, M246DT or M24DD, or a combination thereof, and exhibit strong synergistic effects. Both sexes of adults (ca. 1:1) and nymphs were attracted and captured in traps baited with both murgantiol (MGT) and M246DT/

M24DD, or M246DT/M24DD. During this time, the number of nymphs captured was only 5% of total catches.

It is noted that while these experiments took place in September, it is expected that the results observed will be similar for the time periods of late spring, summer, and late fall.

While illustrative embodiments have been illustrated and described, it will be appreciated that various changes can be made therein without departing from the spirit and scope of the invention.

The embodiments of the invention in which an exclusive property or privilege is claimed are defined as follows:

1. A composition, comprising:
a synergistic combination of murgantiol and at least one of methyl (2E,4Z)-decadienoate, methyl (2E,4E,6Z)-decatrienoate, any stereoisomers thereof, or any combination thereof.

2. The composition of claim 1, further comprising an antioxidant, an oil, or any combination thereof 3. The composition of claim 1, wherein the composition is a brown marmorated stink bug attractant.

4. The composition of claim 1, comprising murgantiol and methyl (2E,4Z)-decadienoate or any stereoisomers thereof.

5. The composition of claim 1, comprising murgantiol and methyl (2E,4Z)-decadienoate.

6. The composition of claim 1, comprising murgantiol and methyl (2E,4E,6Z)-decatrienoate or any stereoisomers thereof.

7. The composition of claim 1, comprising murgantiol and methyl (2E,4E,6Z)-decatrienoate.

8. The composition of claim 1, comprising murgantiol, methyl (2E,4Z)-decadienoate, and methyl (2E,4E,6Z)-decatrienoate.

9. A method of attracting a brown marmorated stink bug, comprising:
providing a trap comprising a composition according to claim 1; and
attracting the brown marmorated stink bug to the trap.

10. The method of claim 9, wherein the brown marmorated stink bug is an adult brown marmorated stink bug.

11. The method of claim 9, wherein the brown marmorated stink bug is a nymph brown marmorated stink bug.

12. The method of claim 9, further comprising trapping the brown marmorated stink bug.

13. A method of attracting a brown marmorated stink bug, comprising:
providing an effective amount of the composition of claim 1 to a predetermined location; and
attracting the brown marmorated stink bug to the predetermined location.

14. The method of claim 13, wherein the brown marmorated stink bug is an adult brown marmorated stink bug.

15. The method of claim 13, wherein the brown marmorated stink bug is a nymph brown marmorated stink bug.

16. The method of claim 13, further comprising trapping the brown marmorated stink bug.

17. The method of claim 13, wherein the predetermined location comprises crop fields, fences, decks, gardens, fruit trees, ornamental trees, orchards, or nurseries.

* * * * *